United States Patent
Yoda et al.

(10) Patent No.: US 9,456,980 B2
(45) Date of Patent: Oct. 4, 2016

(54) LATANOPROST-CONTAINING AQUEOUS PHARMACEUTICAL COMPOSITION

(75) Inventors: Kohei Yoda, Chuo-ku (JP); Satoshi Yamazaki, Saitama (JP); Emi Kawaguchi, Chuo-ku (JP)

(73) Assignee: WAKAMOTO PHARMACEUTICAL CO., LTD., Tokyo (JP)

( * ) Notice: Subject to any disclaimer, the term of this patent is extended or adjusted under 35 U.S.C. 154(b) by 189 days.

(21) Appl. No.: 12/674,962

(22) PCT Filed: Aug. 29, 2008

(86) PCT No.: PCT/JP2008/065564
§ 371 (c)(1),
(2), (4) Date: Feb. 24, 2010

(87) PCT Pub. No.: WO2009/028674
PCT Pub. Date: Mar. 5, 2009

(65) Prior Publication Data
US 2011/0065790 A1 Mar. 17, 2011

(30) Foreign Application Priority Data

Aug. 29, 2007 (JP) .................................. 2007-222316
Jan. 10, 2008 (JP) .................................. 2008-002673

(51) Int. Cl.
| *A61K 9/00* | (2006.01) |
| *A61K 31/5575* | (2006.01) |
| *A61K 31/215* | (2006.01) |
| *A61K 31/557* | (2006.01) |
| *A61K 47/14* | (2006.01) |
| *A61K 47/26* | (2006.01) |
| *A61K 47/44* | (2006.01) |

(52) U.S. Cl.
CPC ......... *A61K 9/0048* (2013.01); *A61K 31/5575* (2013.01); *A61K 31/215* (2013.01); *A61K 31/557* (2013.01); *A61K 47/14* (2013.01); *A61K 47/26* (2013.01); *A61K 47/44* (2013.01)

(58) Field of Classification Search
None
See application file for complete search history.

(56) References Cited

U.S. PATENT DOCUMENTS

| 5,624,962 | A | 4/1997 | Takeuchi et al. |
| 6,235,781 | B1 | 5/2001 | Weiner et al. |
| 7,225,949 | B2 | 6/2007 | Kubo et al. |
| 2004/0082660 | A1* | 4/2004 | Ueno ............................ 514/573 |
| 2004/0253280 | A1 | 12/2004 | Chowhan et al. |
| 2005/0165368 | A1 | 7/2005 | Py et al. |
| 2006/0069162 | A1* | 3/2006 | Asada et al. ................... 514/573 |
| 2006/0211599 | A1 | 9/2006 | Suzuki |
| 2007/0093765 | A1* | 4/2007 | Kawashiro et al. .......... 604/295 |
| 2007/0128156 | A1 | 6/2007 | Chowhan et al. |

FOREIGN PATENT DOCUMENTS

| JP | 2729859 | 12/1997 |
| JP | 2004-166978 | 6/2001 |
| JP | 2002-161037 | 6/2002 |
| JP | 2002-520368 | 7/2002 |
| JP | 2003-95924 | 4/2003 |
| JP | 2004-051170 | 2/2004 |
| JP | 2004-123729 | 4/2004 |
| JP | 2005-160972 | 6/2005 |
| JP | 2006-503913 | 2/2006 |
| JP | 2007-500244 | 1/2007 |
| JP | 2007-511295 | 5/2007 |
| WO | WO 2004/112836 | 12/2004 |
| WO | WO 2005/042026 | 5/2005 |

OTHER PUBLICATIONS

Remington, The Science and Practice of Pharmacy, 21st ed., 2005, pp. 224, 748.*
Written Opinion of the International Searching Authority for PCT/JP2008/065564, mailed Oct. 7, 2008.
Japanese Office Action issued for corresponding Japanese Patent Application No. 2009-530211, dated Mar. 18, 2013.

* cited by examiner

Primary Examiner — Jeffrey S Lundgren
Assistant Examiner — Stephanie Springer
(74) Attorney, Agent, or Firm — Nixon & Vanderhye P.C.

(57) ABSTRACT

The invention provides a latanoprost-containing aqueous pharmaceutical composition filled in a filter-equipped container, with the adsorption of latanoprost by the filter being prevented. In the latanoprost-containing aqueous pharmaceutical composition filled in the filter-equipped container, a nonionic surfactant is contained in the composition and the filter is made from at least one material selected from the group consisting of polyether sulfone, polyvinylidene fluoride, polycarbonate, and polytetrafluoroethylene.

8 Claims, No Drawings

LATANOPROST-CONTAINING AQUEOUS PHARMACEUTICAL COMPOSITION

This application is the U.S. national phase of International Application No. PCT/JP2008/065564 filed 29 Aug. 2008, which designated the U.S. and claims priority to Japan Application No. 2007-222316 filed 29 Aug. 2007, and Japan Application No. 2008-002673 filed 10 Jan. 2008, the entire contents of each of which are hereby incorporated by reference.

TECHNICAL FIELD

The present invention relates to an aqueous pharmaceutical composition filled in a filter-equipped container, comprising latanoprost and a nonionic surfactant.

BACKGROUND ART

Aqueous pharmaceutical compositions including eye drops and the like are required to have sufficient preservatives-effectiveness in order to prevent them from being contaminated by microorganisms during production or use of the compositions. The preservatives-effectiveness is usually checked by the preservatives-effectiveness tests prescribed in the general information of the Japanese Pharmacopoeia.

To impart sufficient preservatives-effectiveness to the aqueous pharmaceutical composition, it has been considered essential to contain the preservatives, in particular, benzethonium chloride, benzalkonium chloride, parabens, chlorobutanol, sorbic acid or their salts, or the like. However, there is a concern that use of some kinds of preservatives may have an adverse effect on some tissues, for example, the cornea or the like. Therefore, it is desirable that aqueous pharmaceutical compositions doesn't contain any kinds of preservatives, or contain them in lower concentration if we have to add some preservatives.

The absence of preservative naturally suggests that the composition will not pass the preservatives-effectiveness tests. There is proposed another method where no preservative is added, i.e., a method of using as containers for holding aqueous pharmaceutical compositions therein a special container, notably, a filter-equipped container or a disposable container (single-unit container). The filter-equipped container can prevent the entry of bacteria into the contents, i.e., constitutionally prevent the contamination of the contents (JP 2004-051170 A and JP 2004-166978 A). The disposable container is discarded once opened and used, so that the polluted container will not be used again even if bacteria are mixed into the contents of the container. The method of using such a filter-equipped container or disposable container is considered remarkably advantageous as the method where no preservative is added to the aqueous pharmaceutical compositions.

However, use of the disposable container will lead to loss of much liquid medication. For convenience in dividing the medication into portions, it is necessary to pack the liquid medication in each container with excess of the single quantity to be used at one time. This is highly disadvantageous, especially for the medication containing expensive raw materials. In addition, some disposable containers are in special shapes or others have to be treated differently from general containers, for example, by discarding the first one drop of medication prior to the use. This may cause various problems in use. In contrast to this, the filter-equipped container has the advantage of being treated in the same manner as in the general containers. This means the users can treat the filter-equipped container without recognizing the filter-equipped container as a special one, which can significantly reduce unexpected troubles.

As previously mentioned, it is considered extremely useful to fill a filter-equipped container with an aqueous pharmaceutical composition free of preservative that may have an adverse effect on some tissues, such as the cornea or the like.

In light of the structure of the container, the aqueous pharmaceutical composition is allowed to pass through the filter installed in the container. Therefore, consideration should be given to the interaction between the ingredients contained in the aqueous pharmaceutical composition and the filter installed in the container. There are some materials that tend to be easily adsorbed by the filter due to their chemical or physical properties. In other words, the compatibility between the aqueous pharmaceutical composition and the material for constituting the filter is important when the aqueous pharmaceutical composition is filled in the filter-equipped container.

SUMMARY OF INVENTION

Technical Problem

An object of the present invention is to provide a latanoprost-containing aqueous pharmaceutical composition filled in a container equipped with a filter, with adsorption of latanoprost to the filter being prevented.

Solution to Problem

The inventors of the present invention intensively investigated the effects of additives contained in the aqueous pharmaceutical composition on the adsorption of latanoprost to the filter. As a result, it has been found that the adsorption of latanoprost to the filter can be significantly prevented when the composition contains a nonionic surfactant and is filled in a container equipped with a filter constructed from a particular material. The invention has thus accomplished.

Accordingly, the invention provides an aqueous pharmaceutical composition shown below.

1. A latanoprost-containing aqueous pharmaceutical composition filled in a container with a filter, characterized in that the composition further comprises a nonionic surfactant and the filter comprises at least one material selected from the group consisting of polyether sulfone, polyvinylidene fluoride, polycarbonate, and polytetrafluoroethylene.

2. The aqueous pharmaceutical composition as described in the above-mentioned item 1, wherein the material for the filter is polyether sulfone.

3. The aqueous pharmaceutical composition as described in the above-mentioned item 1 or 2, wherein the nonionic surfactant comprises at least one selected from the group consisting of polysorbate, polyoxyethylene hydrogenated castor oil, polyoxyl stearate, and polyoxyethylene polyoxypropylene glycol.

4. The aqueous pharmaceutical composition as described in the above-mentioned item 1 or 2, wherein the nonionic surfactant comprises at least one selected from the group consisting of polysorbate 80, polyoxyethylene hydrogenated castor oil 60, polyoxyl (40) stearate, and polyoxyethylene (200) polyoxypropylene glycol (70).

5. The aqueous pharmaceutical composition as described in the above-mentioned item 1 or 2, wherein the nonionic surfactant comprises polysorbate 80 and polyoxyethylene hydrogenated castor oil 60.

ADVANTAGEOUS EFFECTS OF INVENTION

In the latanoprost-containing aqueous pharmaceutical composition filled in a filter-equipped container according to the invention, a nonionic surfactant is contained in the composition and the filter employs a specific material. This has the effect of significantly preventing latanoprost from being adsorbed by the filter.

DESCRIPTION OF EMBODIMENTS

The concentration of latanoprost employed in the composition of the invention, which is not particularly limited as long as the effects of the invention can be obtained, may be preferably 0.0005 to 5 w/v %, and more preferably 0.001 to 1 w/v %.

Any nonionic surfactant(s) can be used in the invention with no particular limitation as long as the effects of the invention can be obtained. Preferably, polysorbate, polyoxyethylene hydrogenated castor oil, polyoxyl stearate and polyoxyethylene polyoxypropylene glycol may be used, and more preferably polysorbate 80, polyoxyethylene hydrogenated castor oil 60, polyoxyl 40 stearate and polyoxyethylene (200) polyoxypropylene glycol (70) may be used, and most preferably polysorbate 80 and polyoxyethylene hydrogenated castor oil 60 may be used.

The concentration of the nonionic surfactant used in the invention is not particularly limited as long as the effects of the invention can be obtained, but may be preferably in the range of 0.0005 to 10 w/v %, and more preferably 0.001 to 5 w/v %.

The material of the container used in the invention is not particularly limited as long as the effects of the invention can be obtained, but may be preferably polypropylene, polyethylene or polyethylene terephthalate, and more preferably polypropylene.

The material of the filter used in the invention is not particularly limited as long as the effects of the invention can be obtained, but preferably may be polyether sulfone (PES), polyvinylidene fluoride (PVDF), polycarbonate, polytetrafluoroethylene (PTFE) or mixed cellulose ester (MSE). In particular, polyether sulfone is more preferable. The commercially available filters made from polyether sulfone include Millipore Express (registered trademark) and Millipore Express (registered trademark) PLUS made by Millipore Corporation, and the like.

There is no limit to pH of the aqueous pharmaceutical composition of the invention as long as the effects of the invention can be obtained, but the pH range of 4 to 10 is preferable. In consideration of irritation to the eyes, the aqueous pharmaceutical composition of the invention may be preferably adjusted to pH 5.0 to 8.0, and more preferably 6.2 to 7.2.

Any pH adjustor can be used with no particular limitation, and phosphates and borates can be used, for example. More specifically, sodium dihydrogen phosphate dihydrate, disodium phosphate dodecahydrate, boric acid, borax and the like can be used.

The osmotic pressure ratio of the aqueous pharmaceutical composition of the invention is not particularly limited as long as the effects of the invention can be obtained, but preferably in the range of 0.1 to 4.0. In consideration of irritation to the eyes, the osmotic pressure ratio may be preferably adjusted to 0.5 to 2.0, and more preferably 0.8 to 1.2.

To adjust the osmotic pressure ratio of the aqueous pharmaceutical composition according to the invention, a variety of isotonic agents generally used may be added. Examples of the ionic isotonic agent include potassium chloride, calcium chloride, sodium chloride, magnesium chloride and the like. Examples of the nonionic isotonic agent include dextrose, xylitol, D-sorbitol, D-mannitol, glycerol, propylene glycol, macrogol 4000 and the like.

The aqueous pharmaceutical composition according to the invention may further comprise sodium edetate or the like as a stabilizer, preferably in an amount of 0.0001 to 0.1 w/v %, and more preferably 0.001 to 0.01 w/v %.

The latanoprost-containing aqueous pharmaceutical composition filled in a filter-equipped container according to the invention is adaptable to any administration route by taking advantage of the characteristics of the composition. The compositions adaptable to local administration to the ears, nose or eyes are desirable, and the compositions prepared for the local administration to the eyes (i.e., eye drops) are most preferable.

EXAMPLES

Test Example 1

0.02 g of benzalkonium chloride was added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper (material: polypropylene) equipped with a filter made from polyether sulfone (Millipore Express (registered trademark) made by Millipore Corporation) and the eye dropper was tightly sealed. Thus, an aqueous pharmaceutical composition was prepared (Comparative Example 1).

Either polysorbate 80 or polyoxyethylene hydrogenated castor oil 60 was added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, aqueous pharmaceutical compositions of the invention were prepared (Examples 1 and 2).

The content of latanoprost in each of the aqueous pharmaceutical compositions prepared in Comparative Example and Examples mentioned above was determined by high-performance liquid chromatography (HPLC). The determination was carried out using three samples: the first drop which was allowed to pass through the filter and drop (hereinafter referred to as "first drop") after the aqueous pharmaceutical composition was prepared and filled in the container, the subsequent drop (hereinafter referred to as "second drop"), and a solution filled in the container (hereinafter referred to as "solution in container"). The adsorption of latanoprost by the filter was evaluated by comparing the HPLC results of the first drop and second drop with solution in container. The results are shown in Table 1.

TABLE 1

| Ingredients (w/v (%)) | | Comparative Example 1 | Example 1 | Example 2 |
|---|---|---|---|---|
| Latanoprost | | 0.005 | 0.005 | 0.005 |
| Sodium dihydrogen phosphate dihydrate | | 0.585 | 0.585 | 0.585 |
| Disodium phosphate dodecahydrate | | 1.2 | 1.2 | 1.2 |
| Benzalkonium chloride | | 0.02 | — | — |
| Polysorbate 80 | | — | 0.5 | — |
| Polyoxyethylene hydrogenated castor oil 60 | | — | — | 0.5 |
| pH of composition | | 6.7 | 6.7 | 6.7 |
| Osmotic pressure ratio of composition | | approx. 1 | approx. 1 | approx. 1 |
| Material for filter: polyether sulfone | | | | |
| Content of Latanoprost (ratio (%) based on the concentration of composition) | Solution in container | 96.7% | 103.6% | 104.5% |
| | First drop (vs. solution in container) | 47.4% (decrease of 50.9%) | 93.1% (decrease of 10.1%) | 93.7% (decrease of 10.3%) |
| | Second drop (vs. solution in container) | 28.7% (decrease of 70.3%) | 105.6% (decrease of 1.9%) | 97.7% (decrease of 6.5%) |

When Examples 1 and 2 are compared with Comparative Example 1, it is found that the adsorption of latanoprost to the filter can be remarkably reduced by adding the nonionic surfactant of the invention to the composition. The decrease of content of latanoprost in the first drop is about 10% in each of Examples 1 and 2. The decrease of the content of latanoprost in the second drop is −1.9% in Example 1. The decrease of the content of latanoprost in the second drop is 6.5% in Example 2. Both in first drop and in second drop, the decreases of the content of latanoprost in Example 1 and Example 2 are lower than that in Comparative Example 1. Those results demonstrate that each nonionic surfactant, polysorbate 80 or polyoxyethylene hydrogenated castor oil 60, can have the effect of the invention.

Test Example 2

0.02 g of benzalkonium chloride was added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition was prepared (Comparative Example 2).

Polysorbate 80 and polyoxyethylene hydrogenated castor oil 60 were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 3).

Polysorbate 80, polyoxyethylene hydrogenated castor oil 60 and polyoxyl 40 stearate were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 4).

Polysorbate 80, polyoxyethylene hydrogenated castor oil 60 and propylene glycol were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 5).

Polysorbate 80, polyoxyethylene hydrogenated castor oil 60, polyoxyl 40 stearate and polyoxyethylene (200) polyoxypropylene glycol (70) were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 6).

The content of latanoprost in each of the aqueous pharmaceutical compositions prepared in Comparative Example and Examples mentioned above was determined by HPLC. The determination was carried out using three samples: the first drop which was allowed to pass through the filter and drop (hereinafter referred to as "first drop") after the aqueous pharmaceutical composition was prepared and filled in the container, the subsequent drop (hereinafter referred to as "second drop"), and a solution packed in the container (hereinafter referred to as "solution in container"). The adsorption of latanoprost by the filter was evaluated by comparing the HPLC results of the first drop and second drop with solution in container. The results are shown in Table 2.

TABLE 2

| | | Comparative Example 2 | Example 3 | Example 4 | Example 5 | Example 6 |
|---|---|---|---|---|---|---|
| Ingredients (w/v(%)) | | | | | | |
| Latanoprost | | 0.005 | 0.005 | 0.005 | 0.005 | 0.005 |
| Sodium dihydrogen phosphate dihydrate | | 0.585 | 0.585 | 0.585 | 0.293 | 0.585 |
| Disodium phosphate dodecahydrate | | 1.2 | 1.2 | 1.2 | 0.6 | 1.2 |
| Benzalkonium chloride | | 0.02 | — | — | — | — |
| Polysorbate 80 | | — | 0.5 | 0.5 | 0.5 | 0.5 |
| Polyoxyethylene hydrogenated castor oil 60 | | — | 0.5 | 0.5 | 0.5 | 0.5 |
| Polyoxyl 40 stearate | | — | — | 0.08 | — | 0.08 |
| Polyoxyethylene (200) polyoxypropylene glycol (70) | | — | — | — | — | 5 |
| Propylene glycol | | — | — | — | 1.4 | — |
| pH of composition | | 6.7 | 6.7 | 6.7 | 6.7 | 6.7 |
| Osmotic pressure ratio of composition | | approx. 1 | approx. 1 | approx. 1 | approx. 1 | approx. 1 |
| Material for filter: polyether sulfone | | | | | | |
| Content of Latanoprost (ratio (%) based on the concentration of composition | Solution in container | 96.7% | 99.4% | 96.5% | 97.5% | 103.3% |
| | First drop (vs. solution in container) | 47.4% (decrease of 50.9%) | 93.0% (decrease of 6.4%) | 85.4% (decrease of 11.5%) | 84.1% (decrease of 13.7%) | 99.0% (decrease of 4.2%) |
| | Second drop (vs. solution in container) | 28.7% (decrease of 70.3%) | 96.7% (decrease of 2.7%) | 91.6% (decrease of 5.0%) | 96.6% (decrease of 0.9%) | 101.9% (decrease of 1.4%) |

When Examples 3 to 6 are compared with Comparative Example 2, it is found that the adsorption of latanoprost by the filter can be remarkably reduced by adding the nonionic surfactant of the invention to the composition. The decrease of the content of latanoprost in the first drop is 4.2 to 13.7%, and in the second drop is 0.9 to 5.0% in Examples 3 to 6. The rate of decrease in the latanoprost content in any of Examples 3 to 6 is obviously lower than that in Comparative Example 2.

Test Example 3

Polysorbate 80 and polyoxyethylene hydrogenated castor oil 60 were added to 50 mL of sterile purified water and dissolved therein. To this solution 0.005 g of latanoprost was added. Then, Sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper (material: polypropylene) equipped with a filter made from mixed cellulose ester (MF-Millipore (registered trademark) made by Millipore Corporation) and the eye dropper was tightly sealed. Thus, an aqueous pharmaceutical composition was prepared (Comparative Example 3).

Polysorbate 80 and polyoxyethylene hydrogenated castor oil 60 were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper (material: polypropylene) equipped with a filter made from polyethylene (Millipore Express (registered trademark) made by Millipore Corporation) and the eye dropper was tightly sealed. Thus, an aqueous pharmaceutical composition was prepared (Comparative Example 4).

Polysorbate 80 and polyoxyethylene hydrogenated castor oil 60 were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 7).

The content of latanoprost in each of the aqueous pharmaceutical compositions prepared in Comparative Examples and Example mentioned above was determined by HPLC. The determination was carried out using three samples: the first drop which was allowed to pass through the filter and drop (hereinafter referred to as "first drop") after the aqueous pharmaceutical composition was prepared and filled in the container, the subsequent drop (hereinafter referred to as "second drop"), and a solution filled in the container (hereinafter referred to as "solution in container"). The adsorption of latanoprost by the filter was evaluated by comparing the HPLC results of the first drop and second drop with "solution in container. The results are shown in Table 3.

TABLE 3

| Ingredients (w/v (%)) | | Comparative Example 3 | Comparative Example 4 | Example 7 |
|---|---|---|---|---|
| Latanoprost | | 0.005 | 0.005 | 0.005 |
| Sodium dihydrogen phosphate dihydrate | | 0.585 | 0.585 | 0.585 |
| Disodium phosphate dodecahydrate | | 1.2 | 1.2 | 1.2 |
| Polysorbate 80 | | 0.5 | 0.5 | 0.5 |
| Polyoxyethylene hydrogenated castor oil 60 | | 0.5 | 0.5 | 0.5 |
| pH of composition | | 6.7 | 6.7 | 6.7 |
| Osmotic pressure ratio of composition | | approx. 1 | approx. 1 | approx. 1 |
| Material for filter | | Mixed cellulose ester | Polyethylene | Polyether sulfone |
| Content of Latanoprost (ratio (%) based on the concentration of composition) | Solution in container | 95.1% | 97.4% | 99.4% |
| | First drop (vs. solution in container) | 61.0% (decrease of 35.8%) | 0.0% (decrease of 100%) | 93.0% (decrease of 6.4%) |
| | Second drop (vs. solution in container) | 81.1% (decrease of 14.7%) | 94.6% (decrease of 2.9%) | 96.7% (decrease of 2.7%) |

When Example 7 is compared with Comparative Examples 3 and 4, it is found that the adsorption of latanoprost by the filter can be remarkably reduced by using the specific material of the filter of the invention. The rate of decrease in the latanoprost content in the first and second drops in Example 7 is obviously lower than that in Comparative Examples 3 and 4. Those results demonstrate that use of the filter especially made from polyether sulfone can have the significant effects of the invention.

Test Example 4

0.02 g of benzalkonium chloride was added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone and the eye dropper was tightly sealed. Thus, an aqueous pharmaceutical composition was prepared (Comparative Example 5).

Polysorbate 80 and polyoxyethylene hydrogenated castor oil 60 were added to 50 mL of sterile purified water and dissolved therein. To this solution 0.005 g of latanoprost was added. Then, sodium dihydrogen phosphate dihydrate and disodium phosphate dodecahydrate were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 8).

Polysorbate 80 and polyoxyethylene hydrogenated castor oil 60 were added to 50 mL of sterile purified water and dissolved therein. To this solution 0.005 g of latanoprost was added. Then, boric acid and borax were separately added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, an aqueous pharmaceutical composition of the invention was prepared (Example 9).

Polysorbate 80 and polyoxyethylene hydrogenated castor oil 60 were added to 50 mL of sterile purified water and dissolved therein. To this solution 0.005 g of latanoprost was added. Then, the combination of sodium dihydrogen phosphate dihydrate and disodium phosphate dodecahydrate, or the combination of boric acid and borax was individually added, and sodium edetate was further added. After the whole solution was confirmed to be clear, sterile purified water was added until the total volume reached 100 mL. The solution thus obtained was transferred to an eye dropper equipped with a filter made from polyether sulfone (Millipore Express (registered trademark) made by Millipore Corporation) and the eye dropper was tightly sealed. Thus, aqueous pharmaceutical compositions of the invention were prepared (Examples 10 and 11).

The content of medication in each of the aqueous pharmaceutical compositions prepared in Comparative Example and Examples mentioned above was determined by HPLC. The determination was carried out using three samples: the first drop which was allowed to pass through the filter and drop (hereinafter referred to as "first drop") after the aqueous pharmaceutical composition was prepared and filled in the container, the subsequent drop (hereinafter referred to as "second drop"), and a solution filled in the container (hereinafter referred to as "solution in container"). The adsorption of latanoprost by the filter was evaluated by comparing the HPLC results of the first drop and second drop with solution in container. The results are shown in Table 4.

TABLE 4

|  | Comparative Example 5 | Example 8 | Example 9 | Example 10 | Example 11 |
|---|---|---|---|---|---|
| Ingredients |  |  |  |  |  |
| Latanoprost | 0.005 | 0.005 | 0.005 | 0.005 | 0.005 |
| Sodium dihydrogen phosphate dihydrate | 0.585 | 0.585 | — | 0.585 | — |
| Disodium phosphate dodecahydrate | 1.2 | 1.2 | — | 1.2 | — |
| Boric acid | — | — | 1.2 | — | 1.2 |
| Borax | — | — | 0.06 | — | 0.06 |
| Benzalkonium chloride | 0.02 | — | — | — | — |
| Polysorbate 80 | — | 0.5 | 0.5 | 0.5 | 0.5 |
| Polyoxyethylene hydrogenated castor oil 60 | — | 0.5 | 0.5 | 0.5 | 0.5 |
| Disodium edetate | — | — | — | 0.005 | 0.005 |
| pH of composition | 6.7 | 6.7 | 6.7 | 6.7 | 6.7 |
| Osmotic pressure ratio of composition | approx. 1 | approx. 1 | approx. 1 | approx. 1 | approx. 1 |
| Material for filter: polyether sulfone |  |  |  |  |  |
| Content of Latanoprost (ratio (%) based on the concentration of composition) — Solution in container | 96.7% | 99.4% | 97.7% | 97.1% | 98.2% |
| First drop (vs. solution in container) | 47.4% (decrease of 50.9%) | 93.0% (decrease of 6.4%) | 86.8% (decrease of 11.1%) | 81.0% (decrease of 16.5%) | 81.5% (decrease of 17.0%) |
| Second drop (vs. solution in container) | 28.7% (decrease of 70.3%) | 96.7% (decrease of 2.7%) | 93.2% (decrease of 4.6%) | 91.6% (decrease of 5.6%) | 91.1% (decrease of 7.2%) |

When Examples 8 and 9 are compared with Comparative Example 5, it is found that the adsorption of latanoprost by the filter can be remarkably reduced by adding the nonionic surfactant to the composition. The decrease of content of latanoprost is 6.4 to 11.1% in the first drop; and less than 5% in the second drop, in Examples 8 and 9, showing that in any case the rate of decrease in the latanoprost content is lower than that in Comparative Example 5. When the results of Example 8 are compared with those of Example 9, there is virtually no difference in the adsorption of latanoprost to the filter. It is found that the effects of the invention can be obtained regardless of the kinds of buffer agents.

When Examples 10 and 11 are compared with Comparative Example 5, it is found that the adsorption of latanoprost to the filter can be remarkably reduced by adding the nonionic surfactants to the composition. Under such circumstances, the effects of the invention can be maintained even though the composition further comprises the stabilizer such as sodium edetate, which is accepted as a pharmaceutical additive.

Formulation Examples

The formulation examples in addition to the above-mentioned examples are shown below.

Formulation Example 1

| Latanoprost | 0.005 (w/v %) |
|---|---|
| Sodium dihydrogen phosphate dihydrate | 0.3 (w/v %) |
| Disodium phosphate dodecahydrate | 0.6 (w/v %) |
| Polysorbate 80 | 0.5 (w/v %) |
| Polyoxyethylene hydrogenated castor oil 60 | 0.5 (w/v %) |
| Propylene glycol | 1.4 (w/v %) |
| Sodium edetate | 0.005 (w/v %) |

Formulation Example 2

| Latanoprost | 0.005 (w/v %) |
|---|---|
| Boric acid | 1.2 (w/v %) |
| Borax | 0.06 (w/v %) |
| Polysorbate 80 | 0.5 (w/v %) |
| Polyoxyethylene hydrogenated castor oil 60 | 0.5 (w/v %) |
| Propylene glycol | 0.5 (w/v %) |

The formulation example 1 and the formulation example 2 are each available as the composition of the eye drop by filled in the filter-equipped container.

The invention claimed is:

1. A latanoprost-containing aqueous pharmaceutical composition filled in a container with a filter, wherein the composition comprises as a nonionic surfactant, a combination of polysorbate 80 and polyoxyethylene hydrogenated castor oil 60 and a material for the filter is polyether sulfone, wherein the composition does not comprise a preservative selected from the group consisting of benzethonium chloride, benzalkonium chloride, parabens, chlorobutanol, and sorbic acid or their salts,
    wherein the concentration of latanoprost in the composition ranges from 0.001 to 1 w/v %, and the concentration of the nonionic surfactant in the composition ranges from 0.001 to 5 w/v %.

2. The aqueous pharmaceutical composition of claim 1, wherein the composition is an eye drop.

3. The aqueous pharmaceutical composition of claim 2, wherein the composition has a pH of 5.0 to 8.0 adjusted by a pH adjustor selected from the group consisting of sodium dihydrogen phosphate dihydrate, disodium phosphate dodecahydrate, boric acid and borax.

4. The aqueous pharmaceutical composition of claim 2, wherein the composition has a osmotic pressure ratio of 0.5 to 2.0 adjusted by a nonionic isotonic agent selected from the group consisting of dextrose, xylitol, D-sorbitol, D-mannitol, glycerol, propylene glycol and macrogol 4000.

5. The aqueous pharmaceutical composition of claim 1, further comprising a pH adjustor selected from the group consisting of sodium dihydrogen phosphate dihydrate, disodium phosphate dodecahydrate, boric acid, borax, and a combination thereof.

6. The aqueous pharmaceutical composition of claim 5, wherein the pH adjustor is contained so that the pH of the composition becomes 4 to 10.

7. The aqueous pharmaceutical composition of claim 1, further comprising a nonionic isotonic agent selected from the group of consisting of dextrose, xylitol, D-sorbitol, D-mannitol, glycerol, propylene glycol, macrogol 4000, and a combination thereof.

8. The aqueous pharmaceutical composition of claim 7, wherein the nonionic isotonic agent is contained so that the osmotic pressure ratio of the composition becomes 0.1 to 4.0.

* * * * *